United States Patent [19]

Ferber

[11] Patent Number: 4,807,301

[45] Date of Patent: Feb. 28, 1989

[54] PROTECTIVE GARMENT FOR THE HIP AREA

[76] Inventor: Robert C. Ferber, Box 909, Jackson Heights, N.Y. 11372

[21] Appl. No.: 92,209

[22] Filed: Sep. 2, 1987

[51] Int. Cl.⁴ .......................................... A41D 13/00
[52] U.S. Cl. .............................................. 2/2; 2/267; 450/150
[58] Field of Search ................ 128/132 R, 95.1, 99.1; 2/2, 23, 267, ; 450/150

[56] References Cited

U.S. PATENT DOCUMENTS

| | | | |
|---|---|---|---|
| 0.522,967 | 7/1894 | Chapman et al. | 128/99.1 X |
| 1,685,452 | 9/1928 | Goldsmith | 2/23 |
| 1,774,739 | 9/1930 | Voyne | 2/2 |
| 2,481,291 | 9/1949 | Coleman | 2/2 X |
| 2,889,830 | 6/1959 | Raymond | 2/2 X |
| 3,526,221 | 9/1970 | Garber | 128/95.1 |
| 3,801,984 | 4/1974 | Kanicki | 2/2 |
| 3,909,847 | 10/1975 | Holt et al. | 128/132 R |
| 4,128,902 | 12/1978 | Siebert | 2/2 |
| 4,462,115 | 7/1984 | Carlson | 2/2 |
| 4,573,216 | 3/1986 | Wortberg | 2/2 |
| 4,641,641 | 2/1987 | Strock | 128/132 R |
| 4,737,994 | 4/1988 | Galton | 2/2 |
| 4,761,834 | 8/1988 | Kolb | 2/267 X |

OTHER PUBLICATIONS

Journal of AMA vol. 168, No. 7, 19 Oct. 1958, copy in 2/DIG. 6.

Primary Examiner—Louis K. Rimroot

[57] ABSTRACT

A shock stress protective garment is in a size-adjustable wrap-around form and includes pockets with shock-absorbent pads protecting the hips against the normal stress of falling. The shock stress protective garment is also adapted to fit under the buttocks and be worn under normal outer clothing.

10 Claims, 3 Drawing Sheets

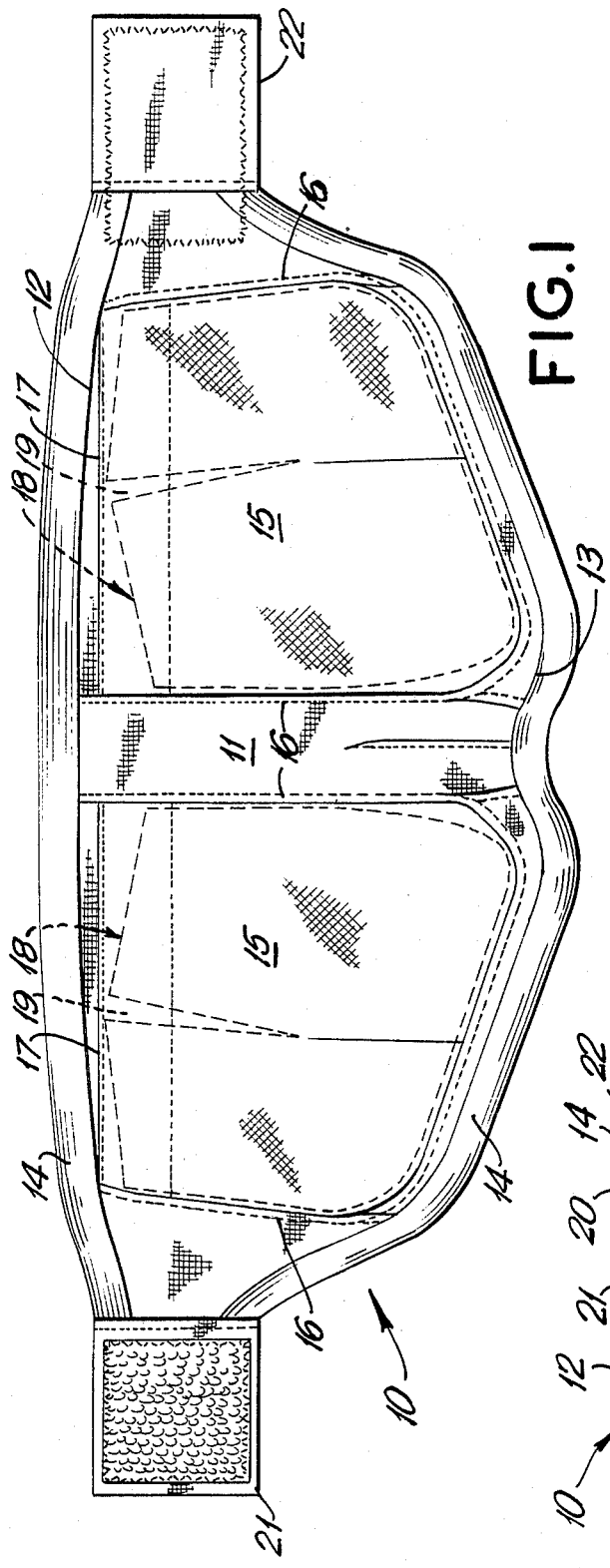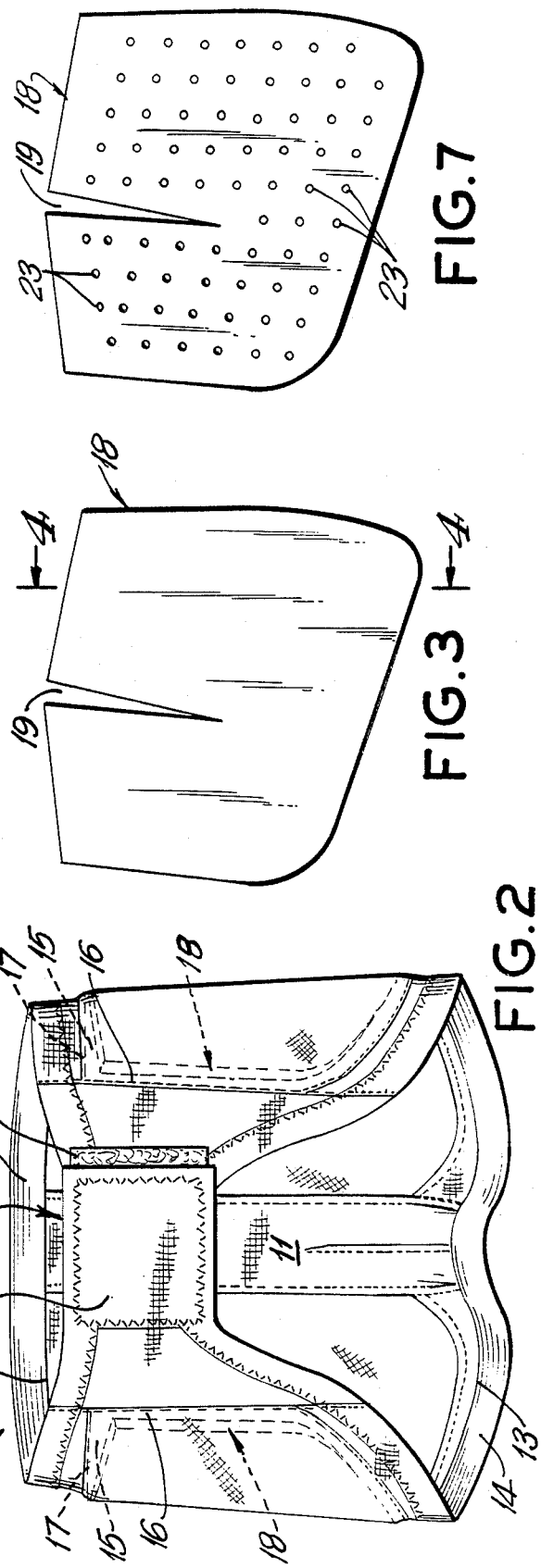

PROTECTIVE GARMENT FOR THE HIP AREA

BACKGROUND OF THE INVENTION

This invention relates to a shock stress protective garment for the hip area, and more particularly, to a shock stress protective garment which may be worn comfortably on the body and which will disperse forces directed toward the hip area, absorbing such forces in the particularly vulnerable regions of the hip.

There are over 300,000 hip fractures suffered by humans each year, in the United States alone, plus uncounted numbers of other hip joint injuries which result in pain. Complications such as pneumonia can result in death, disruption of normal life and substantial medical cost. These fractures and other injuries are particularly common in elderly people, who experience degenerative changes in bone and tissue structure with advancing age. The degenerative changes become far worse after a hip fracture. In view of the fact of ever increasing life expectancies, the number of these injuries and the costs associated with them can only increase with time.

The hip joint is an enarthrodial or ball-and-socket joint formed by the reception of the ball-shaped head on the upper or proximal end of the femur into the cup-shaped cavity in the pelvis called the acetabulum. A fall or blow to the hip bone area, if it is unprotected, can result in body tissue injuries, in dislocation of the femur head from the acetabulum, and/or in fractures of the acetabulum or various parts of the proximal femur or other damages in the proximity. Particularly vulnerable is the so-called greater trochanter which protrudes outwardly from the proximal femur just below the joint and the adjoining thin neck of the femur. This region is relatively poorly protected by muscle and other body tissue in comparison with the regions of the hip which surround it. In fact, the greater trochanter is readily accessible to the touch, its position being generally indicated by an elevation in the hip area, owing to the thinness of the tissues which cover this bone.

The present invention further, while protecting the hip area in particular, comfortably extends protection to the whole pelvic bone area and buttocks at the same time.

The primary problem is that the prior garments which are capable of providing protection are generally difficult to apply and uncomfortable to wear. An effective hip area shock stress protective garment has simply not been available which is sufficiently comfortable to wear for extended periods of time, under clothing, including through normal daytime activities, as well as sleeping at night. The garment of the present invention overcomes prior problems and is so thin that it is not cosmetically disturbing.

In the prior art, U.S. Pat. No. 4,641,641 discloses an annular pad of resilient material that carries adhesive strips on one surface to secure the pad directly to the skin and a dome-shaped shield. U.S. Pat. No. 4,573,216 discloses a pad which protects only small, isolated areas, such as the immediate area where the greater trochanter approaches the surface. It depends on adhesive to fix it to the skin, which is never comfortable for long. U.S. Pat. No. 2,889,830 is designed to protect only the area of the greater trochanter. Furthermore, it is bulky in design and uncomfortable, in view of its hard component parts and straps. The same may be said of U.S. Pat. No. 3,526,221. It also protects only the area of the greater trochanter and is designed in such a way that it will quickly be uncomfortable when put on. U.S. Pats. No. 1,756,358 and 1,774,739 are hard, uncomfortable devices worn under clothing designed primarily for sports.

The prior art patents deal with protection of the hip, but do not solve the problem of providing an effective, light, comfortable hip protective garment.

Accordingly, a primary object of the present invention is to provide a shock stress protective garment which serves to reduce the likelihood of fracture or other injury of the hip or surrounding area.

Another object of this invention is to provide a shock stress protective garment which can be worn and removed with ease and without the need of straps, bandages or other devices that are difficult to manipulate and apply, especially by older people with arthritic or weak hands.

Another object of this invention is to provide a shock stress protective garment for the hip area which is lightweight and comfortable to wear for extended periods of time.

Another object of this invention is to provide a shock stress protective garment for the hip area which is capable of adjusting to changes in body position when worn, thereby adding to its comfort, particularly while the wearer is active.

Another object of this invention is to provide a shock stress protective garment for the hip area which is designed to be relatively unobtrusive physically and cosmetically, and comfortable even when the wearer reclines on it, as when sleeping.

Another object of this invention is to provide a shock stress protective garment whose shock absorbent padding will not absorb moisture.

Another object of this invention is to provide a shock stress protective device that can be worn over underwear and under outer clothing, so as to be just about invisible.

Another object of this invention is to protect the entire hip area by means of a wrap-around configuration that is washable, held on by soft, gentle, partially elastic fabric, with shock absorbent padding which is ventilated.

Another object of this invention is to provide a shock stress protective device that the user can wear and be able to sit in comfortably with the bottom of each shock absorbent pad curved around, and between the seat and the user.

A BRIEF SUMMARY OF THE INVENTION

According to the present invention, a girdle-like device in a wide belt configuration is fastened around the body so as to surround the hip area elastically. The device becomes narrower in front and is fastened by means of overlapping strips of Velcro®. It is, therefore, easily fastened and unfastened, particularly by elderly people. When in place, the device is situated somewhat lower than the waist. On each side there is a pocket. The pockets are made of a fairly strong woven, non-stretch material. The pockets hold protective shock absorbent pads in position. The light, thin two-way stretch material holds the device in place when a Velcro® closure is pulled tightly enough. The device is trimmed with stretch lace to better hold it in place, improve its looks and make it to better conform to body contours.

The shock stress protective garment of the present invention comprises a fabric panel which encircles the pelvic area. The panel includes at least one pocket and a closure to fix the shock stress protective garment encircling the pelvic area shock absorbent pad in the pocket. The shock stress protective garment can be worn under normal outer clothing. The fabric panel is preferably a two-way stretch fabric which may extend below the buttocks and includes a lower elastic edge.

The closure is preferably Velcro ® and long enough to be longitudinally adjustable to fit a variety of hip sizes. By closing the Velcro ® ends at an angle, the protective garment may be made to conform to different body contours. Preferably, there are two pockets on the portion of the panel adjacent the body of the wearer at the hip area, including shock absorbent pads and preferably, the shock absorbent pads are perforated with perforations spaced approximately an inch apart. The shock absorbent pads preferably include darts and are preferably of a closed cell plastic construction. The shock absorbent pads are preferably approximately three-eighths to one half inch thick and do not bottom at the hip under the falling stress of normal body weight from a height of two feet.

The wrap-around configuration does much more than previous devices intended for hip area protection, namely, it protects the area around each side of the pelvic circle, where the greater trochanter comes closest to the surface of the body, and it also protects the other fairly exposed bones of the hip area, that is, the ilium, the ischium and the sacrum. The protection is afforded by a closed cell plastic material with tremendous shock-absorbing capability. The closed cell construction means that body fluids such as perspiration or accidental urine will not be absorbed. The shock absorbent padding material can be washed or sponged off, while the garment device can be hand or machine washed. The shock absorbent padding material is soft to the touch, and is made to conform to the rounded body parts by darts cut into the shock absorbent padding material, as well as by the bending ability of the material itself.

Although such novel feature or features believed to be characteristic of the invention are pointed out in the claims, the invention and the manner in which it may be carried out may be further understood by reference to the description following and the accompanying drawings.

Referring now to the figures in greater detail, where like reference numbers denote like parts in the various figures.

BRIEF DESCRIPTION OF THE DRAWINGS

FIG. 1 is a front elevation of the shock stress protective garment of the present invention outstretched.

FIG. 2 is a front elevation of the present invention and folded as if about a body.

FIG. 3 is an elevation of a shock absorbent pad of the present invention.

FIG. 7 is a preferred embodiment of the shock absorbent pad of FIG. 4, including vent holes.

Referring now to the figures in greater detail, where like reference numbers denote like parts in the various figures.

DETAILED DESCRIPTION

Figure 4:
FIG. 4 is a section of FIG. 3, at lines 4—4.
Figure 5:
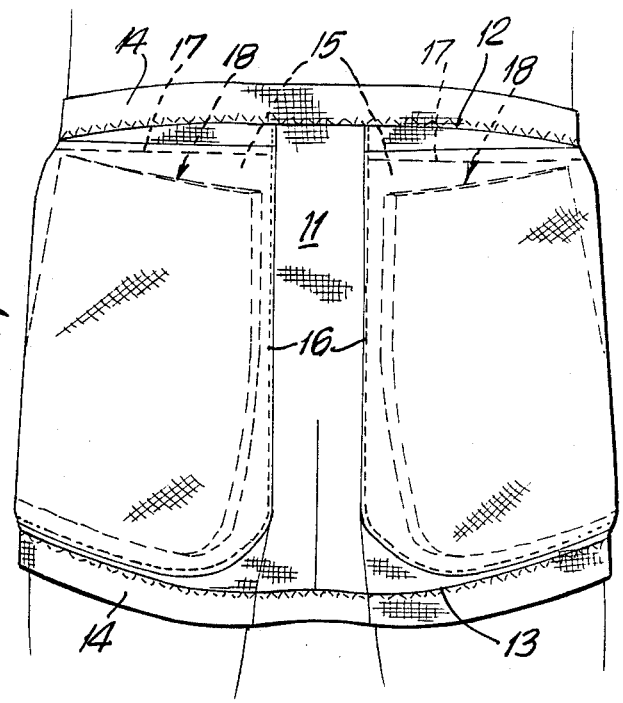
FIG. 5 is a rear elevation of the shock stress protective garment of the present invention shown worn over the hips and buttocks.
Figure 6:
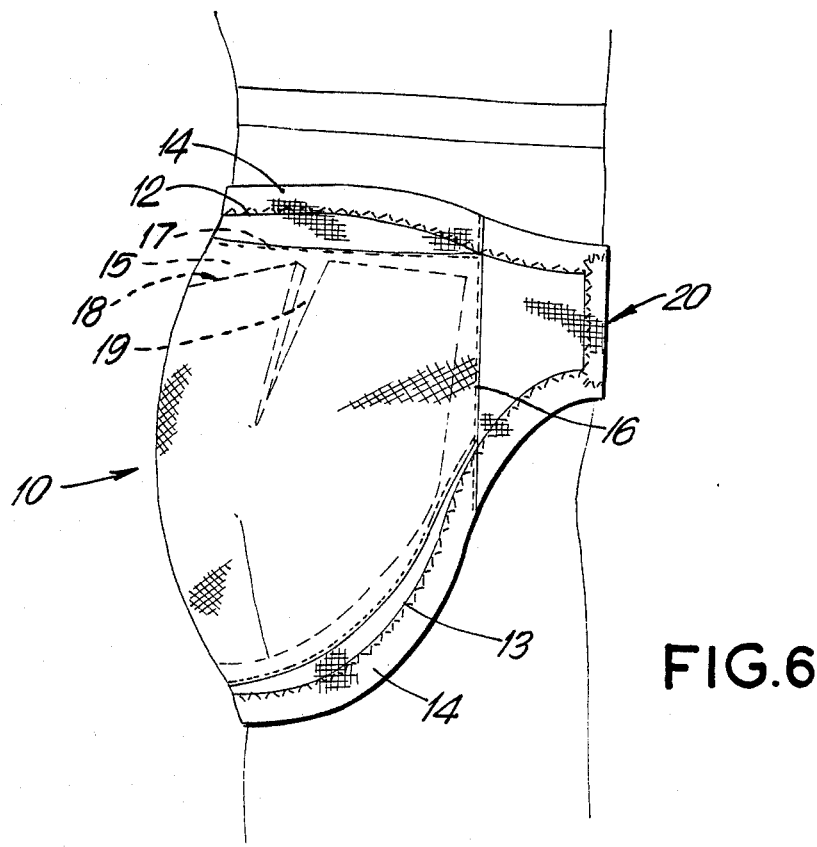
FIG. 6 is a side elevation of the shock stress protective garment of the present invention being worn.
Figure 8:
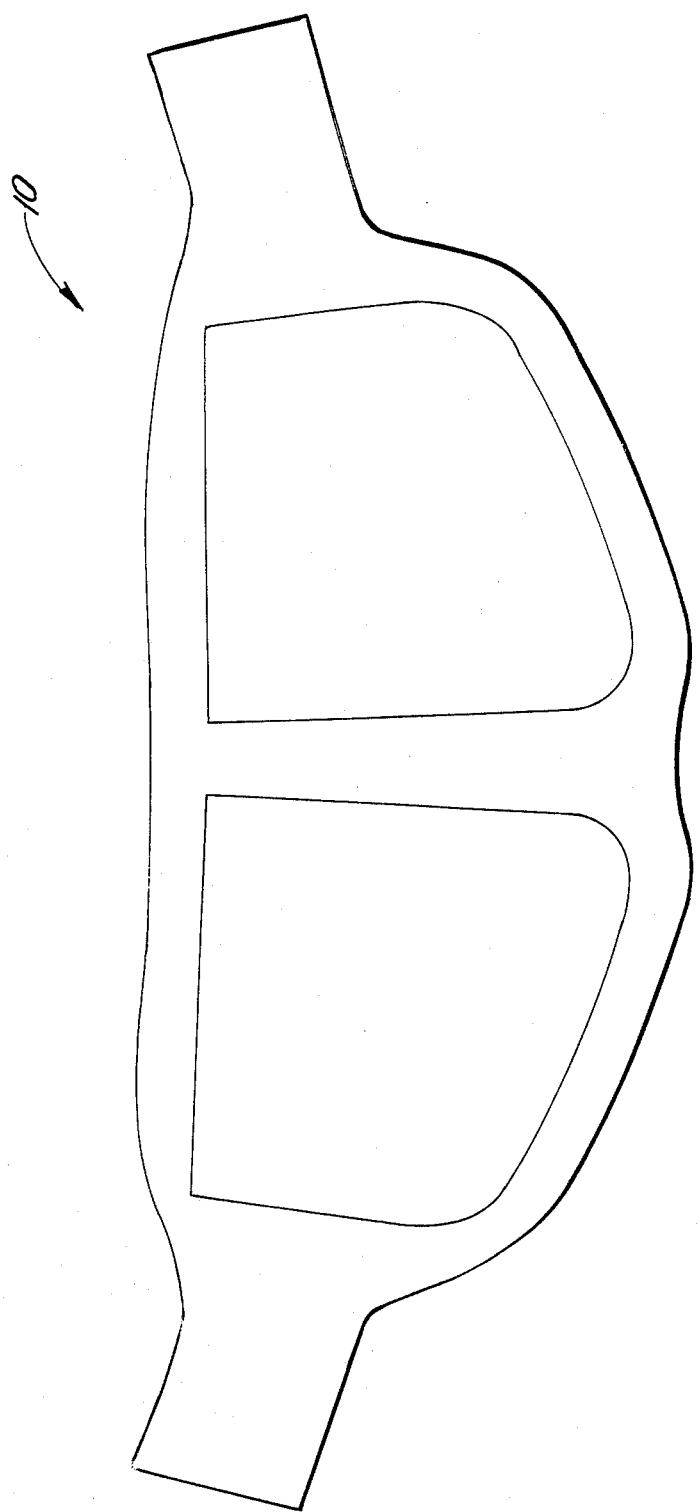
FIG. 8 is a front elevation of the overall garment shape.

The shock stress protective garment 10 in a preferred embodiment has a fabric panel 11, preferably of a thin, two-way stretch material. The fabric panel 11 has an upper edge 12 and a curved lower edge 13, which are trimmed with a stretch lace 14 to improve the looks of the shock stress protective garment 10, and to help it conform to body contours and hold it in place.

Superposed on the inside of the fabric panel 11 are a pair of pockets 15, preferably of a woven non-stretch material, attached by stitching 16. The pockets 15 are open at their upper ends 17 and adapted to receive shock absorbent pads 18. The shock absorbent pads 18 have darts 19 to help the shock absorbent pads 18 adapt to the contours of the body.

The shock stress protective garment 10 is engaged about the body by means of a two-part closure 20 extending from the ends of the fabric panel 11. The two-part closure 20 includes a first part 21 and a second part 22, which are adapted to selectively engage each other over a wide range along their length, to adapt to tightening the shock stress protective garment 10 to different or changing girth sizes. As shown in a preferred embodiment, the two-part closure 20 is a Velcro ® closure with a first part 21 comprising an interengageable matting and the second part 22 having interengageable hooks on its underside.

The shock absorbent pads 18 comprise a non-allergenic PVC nitrile with a closed cell, which makes the shock absorbent pads non-absorbent of fluids. The surface of the shock absorbent pads 18 are smooth so that the shock absorbent pads 18 are easy to insert into and remove from the fabric panel 11 when the shock stress protective garment 10 needs to be washed.

The shock absorbent pads 18, preferably seven-sixteenth to one half of an inch in thickness, which adapts a shock absorbent pad to be effective for people weighing up to 180 pounds, with the shock absorbing capability of not bottoming in a drop of approximately two feet. The stress on the shock absorbent padding material in the drop should not exceed 225 pounds per square inch.

In the preferred embodiment, Sportcell padding, seven-sixteenth of an inch thick, was provided by Freeland & Associates of Port Richey, Fla.

In FIG. 7, the shock absorbent pad 18 is provided with perforations 23, spaced approximately an inch apart. These perforations 23 help ventilate the covered area to avoid unnecessary heat, perspiration, irritation and excessive weight of the shock stress protective garment 10. In use, the shock stress protective garment 10 is wrapped around the lower portion of the waist, below the belt line, over the normal undergarments of the wearer. The first and second parts 21 and 22 of the closure 20 allow a latitude in tightening the shock stress protective garment 10 over the body so that it is both secure and comfortable. The elasticity of the stretch lace 14 on the lower edge 13 holds the lower edge extending beneath the buttocks. Thus, in a reclining or sitting position, the shock absorbent pads 18 comfortably roll up underneath the buttocks.

The downward extension of the lower edge extends the protective area of the shock stress protective garment 10 of the present invention to include other parts of the pelvic bone area, which may also be vulnerable to injury.

The shock absorbent pads 18 conform to the shape of the pockets 15. The pockets 15 follow the contour of the lower edge 13 of the fabric panel 11.

The darts 19 in the shock absorbent pads 18 provide a flexibility for the shock stress protective garment 10 to be comfortably and snugly wrapped around the hip of the wearer.

The closed cells of the shock absorbent pads 18 and their smooth surface make them easily cleanable and non-absorbent to foreign substances, which might contaminate the shock absorbent pads 18.

In use, the shock stress protective garment 10 of the present invention is placed about the body with the shock absorbent pads 18 covering the hips. The closure 20 is adjusted so that the first part 21 and second part 22 engage to adjust the shock stress protective garment 10 to snugly fit around the body. The size of the first and second parts 21, 22 of the closure 20 allow latitude for obtaining a proper closure for people of different sizes.

The darts 19 permit a snug fitting of the shock absorbent pad over the hip area, conforming to its shape. The shock stress protective garment 10 preferably sits below the belt line and is, therefore, worn comfortably under a skirt or pants. Pulled by the stretch lace 14, the lower portion of the shock stress protective garment 10 substantially conforms to the shape of the buttocks and is pulled close in beneath it.

The shock absorbent pads 18 preferably have perforations 23, which reduce the weight of the shock absorbent pad 18, and also provide ventilation for the comfortable wearing of the shock stress protective garment 10.

It is preferable that the pockets 15 and shock absorbent pads 18 be on the inside portion of the fabric panel 11. This helps the entire conformity of the shock absorbent pads 18 to the hips, pulled by the two-way stretch material of the fabric panel 11.

The shock stress protective garment 10 is easily cleaned. The shock absorbent pads 18 are removed so that the shock stress protective garmet 10 may be washed. The shock absorbent pads 18 themselves with their closed cell structure, are easily cleanable and are non-absorbent. The smooth surface of the shock absorbent pads 18 make them easily insertable and removable from the pockets 15.

The padding for the shock absorbent pads 18 is preferably lightweight and thin. It is selected to have particular characteristics so that it does not "bottom", lose its full capacity to perform as a shock absorber, without properly protecting the shock anticipated to be received by a hip joint upon a fall.

Sportcell padding provided by Freeland & Associates of Port Richey, Fla., made of a closed cell PVC nitrile has been found satisfactory on test. A three-eighth thickness was found to provide adequate protection in most cases. Preferably for the purpose of extra safety, a seven-sixteenth inch thickness should be used. Testing of the padding comprised the use of a five-pound steel cylinder of 2.4 square inches cross-sectional area, dropped on a sample from twenty-four inches.

There is no direct way of testing the effectiveness of this invention in vivo. One cannot, in good conscience, give on hundred elderly people samples of the present invention with one thickness of protective material and one hundred with another thickness and cause them to fall to see to what extent the one group is better protected than the other.

What has been done instead, for the purpose of developing a safe garment, is the following: Reports by the Society of Automotive Engineers (STAPP Reports (SAE 885)), show the approximate threshold force that is required to fracture hips of test cadavers. Cadavers do not have the additional protection of surrounding elastic tissue that live people have. Therefore, to assume forces in terms of cadavers, makes it even safer for live people.

The material used for the pads in this invention was picked to absorb sufficient shock during a fall to bring the force down to far below the size described in the SAE tests. The padding material was tested by U.S. Testing Co. and at Wayne State University. The test consisted of dropping steel missiles on the material and measuring the force absorbed by the material. The force generated by a person's falling can be calculated, knowing height of fall and weight of person.

When the garment described in this invention has been used in practice, statistical analyses of effectiveness can be performed.

At present, one may safely say, from the calculations, that 75-90 per cent of persons weighing 140 pounds are protected by the invention from fracture, assuming lack of severe osteoporosis and lack of fracture due to fortuitous twisting of the pelvic frame.

The terms and expressions which are employed are used as terms of description; it is recognized, though, that various modifications are possible.

It is also understood the following claims are intended to cover all of the generic and specific features of the invention herein described; and all statements of the scope of the invention which as a matter of language, might fall therebetween.

Having described certain forms of the invention in some detail, what is claimed is:

1. A shock stress protective garment for the hip area and which is worn around the body at hip level to protect the hips and other bones in the pelvic area from fracture due to impact of falling and which does not contain rigid or semi-rigid plates adjacent the hip or pelvic area comprising a two way stretch fabric panel adapted to extend below the buttocks, said panel adapted to encircle the pelvic area, said panel including at least one pocket located on the portion of the panel adapted to be adjacent the hip bone and pelvic area of the body of the wearer, means to fix said shock stress protective garment encircling the pelvic area, and at least one perforated closed cell plastic shock absorbent pad in said at least one pocket, said pad adapted to extend below the buttocks, the thickness of said shock absorbent pad being from about three-eighths inch to about one-half inch, and said pad is adapted not to bottom under the falling stress of normal body weight from a height of two feet.

2. The invention of claim 1 wherein said shock stress protective garment is adapted to be worn under normal outer clothing.

3. The invention of claim 1 wherein said fabric panel includes at least a lower elastic edge.

4. The invention of claim 1 wherein said fabric panel includes a lower elastic edge.

5. The invention of claim 1 wherein said means to fix is a two piece interengageable fabric closure.

6. The invention of claim 5 wherein said two piece interengageable fabric closure is adapted to be adjusted, whereby said shock stress protective garment is adapted to selected body contours.

7. The invention of claim 1 wherein said panel includes two pockets adjacent the hip area.

8. The invention of claim 7 wherein each said pocket includes one of said shock absorbent pads.

9. The invention of claim 1 wherein said perforations are spaced approximately an inch apart.

10. The invention of claim 1 wherein said at least one shock absorbent pad includes a dart.

* * * * *